United States Patent
Dayan et al.

(10) Patent No.: US 9,103,763 B2
(45) Date of Patent: Aug. 11, 2015

(54) SYSTEM AND METHOD FOR DETECTION OF FOREIGN SUBSTANCES

(75) Inventors: Lev Dayan, Ramat Sharet (IL); Moshe Shalom, Herzeliya (IL); Vitaly Strokhin, Beer-sheva (IL); Vladimir Sergeyev, Rehovot (IL)

(73) Assignee: M.S. TECH LTD., Herzlyia (IL)

( * ) Notice: Subject to any disclaimer, the term of this patent is extended or adjusted under 35 U.S.C. 154(b) by 1331 days.

(21) Appl. No.: 12/739,362

(22) PCT Filed: Oct. 25, 2007

(86) PCT No.: PCT/IL2007/001285
§ 371 (c)(1),
(2), (4) Date: Apr. 22, 2010

(87) PCT Pub. No.: WO2009/053957
PCT Pub. Date: Apr. 30, 2009

(65) Prior Publication Data
US 2010/0305556 A1 Dec. 2, 2010
US 2011/0184397 A2 Jul. 28, 2011

(51) Int. Cl.
*G01N 1/22* (2006.01)
*G01N 29/036* (2006.01)
*G01N 33/00* (2006.01)

(52) U.S. Cl.
CPC .......... *G01N 29/036* (2013.01); *G01N 33/0057* (2013.01); *G01N 2291/0257* (2013.01)

(58) Field of Classification Search
CPC ...... G01N 1/22; G01N 1/42; G01N 2030/025
USPC .............................................. 73/863.11, 23.4
See application file for complete search history.

(56) References Cited

U.S. PATENT DOCUMENTS

| | | | |
|---|---|---|---|
| 4,535,639 A * | 8/1985 | Bianchini et al. | 73/863.11 |
| 6,073,499 A | 6/2000 | Settles | |
| 6,167,747 B1 | 1/2001 | Koch et al. | |
| 6,526,828 B1 | 3/2003 | Dayan et al. | |
| 6,708,572 B2 | 3/2004 | Jenkins et al. | |
| 6,831,273 B2 | 12/2004 | Jenkins et al. | |
| 6,837,095 B2 | 1/2005 | Nakayama et al. | |
| 6,840,122 B1 | 1/2005 | Jenkins et al. | |
| 7,188,513 B2 * | 3/2007 | Wilson | 73/31.05 |
| 7,335,336 B1 | 2/2008 | Kim | |
| 2001/0042413 A1 * | 11/2001 | Sakairi et al. | 73/863.11 |
| 2003/0085348 A1 * | 5/2003 | Megerle | 250/287 |
| 2004/0069046 A1 * | 4/2004 | Sunshine et al. | 73/23.34 |
| 2009/0200458 A1 * | 8/2009 | Kashima et al. | 250/282 |

FOREIGN PATENT DOCUMENTS

WO 2004/057319 A1 7/2004

* cited by examiner

*Primary Examiner* — Hezron E Williams
*Assistant Examiner* — Rodney T Frank
(74) *Attorney, Agent, or Firm* — Browdy and Neimark, PLLC

(57) ABSTRACT

A sensing unit is presented for use in identifying at least one foreign substance in a region of interest. The sensing unit comprises at least one measurement unit, which comprises one or more sensor elements each configured and operable to be responsive to at least one foreign substance in the vicinity thereof. Each sensor element is mounted in its own compartment having an inlet and an outlet thus defining an environmental region in the vicinity of the sensor element separated from the surroundings of the compartment.

40 Claims, 10 Drawing Sheets

SYSTEM AND METHOD FOR DETECTION OF FOREIGN SUBSTANCES

FIELD OF THE INVENTION

This invention is generally in the field of "electronic nose" and "electronic tongue" devices, and relates to a method and system for detection of various substances within a gas or liquid medium or combination of such media.

BACKGROUND OF THE INVENTION

An "electronic nose" is known as a device formed by one or more sensor and a pattern recognition routine. An "electronic tongue" is a device similar to the electronic nose, but capable of operating in a liquid medium, and enables the analysis of solutes in a solution.

Various types of such devices have been developed and are described for example in the following publications:

U.S. Pat. No. 6,167,747 discloses a vapor recovery system that utilizes a crystal oscillator for sensing the presence of hydrocarbon in the vapor emissions emanating from a fuel tank during refueling. The crystal oscillator is coated with a layer of material having sensitivity for hydrocarbon. In response to any interaction between the coating layer and hydrocarbon, the crystal oscillator experiences a shift in its oscillation frequency relative to the fundamental resonance frequency. The frequency shift is representative of the hydrocarbon concentration in the vapor emissions. A control signal based on the frequency shift is generated and then used to adjust the operating speed of the vapor pump.

U.S. Patent Publication No. 2004/0069046A1 discloses a portable vapor sensing device conveniently adapted for use in sensing the presence and concentration of a wide variety of specified vapors. The device provides these benefits using a sensor module that incorporates a sample chamber and a plurality of sensors located on a chip releasably carried within or adjacent to the sample chamber. Optionally, the sensor module can be configured to be releasably plugged into a receptacle formed in the device. Vapors are directed to pass through the sample chamber, whereupon the sensors provide a distinct combination of electrical signals in response to each. The sensors of the sensor module can take the form of chemically sensitive resistors having resistances that vary according to the identity and concentration of an adjacent vapor. These chemically sensitive resistors can each be connected in series with a reference resistor, between a reference voltage and ground, such that an analog signal is established for each chemically sensitive resistor. The resulting analog signals are supplied to an analog-to-digital converter, to produce corresponding digital signals. These digital signals are appropriately analyzed for vapor identification.

WO 04/057319 discloses a piezoelectric sensor arrangement for analysis of fluid samples. The sensor arrangement includes a signal source, a measuring device and a docking system, which comprises a first part provided with means for receiving a sensor element that exposes a piezoelectric quartz crystal and a second part comprising fluid channels for the sample and a flow cell element, which preferably is removable and which comprises a recess, and inlet and outlet fluid channels for leading a fluid through the recess. The first and second parts are movable in relation to each other between a closed position and an open position and are arranged such that in the closed position the recess of the flow cell element is sealingly covered by the piezoelectric quartz crystal so that a flow cell is formed by said flow cell element and said quartz crystal.

U.S. Pat. No. 6,073,499 discloses a portal for use with a detector for detecting trace amounts of contraband that may be retained on skin or clothing of the human subject. The portal relies upon the continuous process by which microscopic flakes of skin continuously separate from human subjects. The portal further relies upon the existence of a human thermal plume consisting of a layer of warm air adjacent the all human subject. The warm air rises in the cooler surrounding air and transports the microscopic flakes of skin upwardly. The portal capitalizes on this phenomenon by providing at least a partial enclosure with a funnel-shaped collector above the human subject. A low speed flow of relatively dense cool air may be introduced into the portal to buoyantly lift the warmer air of the human thermal plume upwardly. The air stream defined by the human thermal plume and the skin particles therein moves to a trap in the funnel-shaped collector above the portal. The trap cooperates with a detector for detecting the presence of molecules of interest.

U.S. Pat. No. 6,831,273 discloses an apparatus for detecting whether substances of interest are present in a sample of air. The apparatus includes a detector, such as an ion trap mobility spectrometer. The detector is operated at a high drift voltage and then is switched to a low drift voltage. Spectra are collected at the high and low field strengths and are compared with standard spectra at those strengths to determine whether materials of interest are present.

U.S. Pat. Nos. 6,708,572 and 6,840,122 disclose portal trace detection systems for detection of imbedded minute particles of interest, such as traces of narcotics, explosives and other contraband. The apparatus includes a portal through which a human suspect will pass. A detection apparatus is disposed at least partly in the ceiling of the portal, and hence above the human subject in the portal. Particles of interest will be entrained in the human thermal plume that exists in the boundary layer of air adjacent the suspect, and will flow upwardly from the suspect to the detection apparatus in the ceiling of the portal. The portal includes a plurality of vertically aligned arrays of air jets. The air jets are fired sequentially from bottom to top to produce short bursts of air sufficient to disturb the clothing of the suspect and to dislodge particles of interest from the clothing. The dislodged particles of interest are entrained in the air in the human thermal plume and are transported upwardly to the detector.

U.S. Pat. No. 6,526,828, assigned to the assignee of the present application, discloses sensitive and selective method and device for the detection of trace amounts of a substance. The device includes a piezoelectric crystal element comprising at least one crystal resonator in the form of an inverted mesa structure, which has a membrane-like region and is characterized by a certain resonance frequency value. A surface region of the crystal resonator is modified by reactive molecules of a kind capable of interacting with the foreign material to yield a reaction product that effects a change in the resonance frequency of the crystal resonator from said certain resonance frequency value. This change is indicative of the identity and quantity of the foreign material.

SUMMARY OF THE INVENTION

There is a need in the art for a quick and effective technique for identifying one or more analytes in a medium, such as air vapor or liquid, providing a novel "electronic nose" or "electronic tongue" method and system.

The present invention provides a sensing system for identifying at least one foreign material in a region of interest. The sensing system includes a predetermined number of sensor units. The sensor unit comprises at least one measurement unit including one or more sensor element (e.g., an array of sensor elements). According to the invention, the sensor element is preferably mounted in its own compartment thus separating the closest environment of the sensor element from the surroundings. This increases the concentration of a sample medium to be inspected when supplied to the sensor element. When using at least two sensor elements, each sensor element is mounted in its own compartment separated from at least one other compartment containing at least one other sensor element. The sensor element is configured and operable to be responsive to at least one foreign material in its surroundings and generating a response signal.

According to one broad aspect of the invention, there is provided a sensing system for use in identifying at least one foreign substance in a region of interest, the sensing system comprising a certain number of sensor units, the sensor unit comprising at least one measurement unit including one or more sensor elements configured and operable to be responsive to at least one foreign substance in the vicinity thereof and to generate a response signal indicative thereof, the sensor element being mounted in its own compartment having an inlet and an outlet thus defining an environmental region in the vicinity of the sensor element separated from the surroundings of the compartment.

According to another broad aspect of the invention, there is provided a sensing system for use in identifying at least one foreign substance in a region of interest, the sensing system comprising a certain number of sensor units, the sensor unit comprising at least one measurement unit comprising an array of at least two sensor elements each configured and operable to be responsive to at least one foreign substance in the vicinity thereof and to generate a response signal indicative thereof, each sensor element being mounted in its own separate compartment having an inlet and an outlet thus defining an environmental region in the vicinity of the sensor element separated from the surroundings of the compartment and from at least one other compartment containing at least one other sensor element.

The system may include more than one sensor unit, more preferably several sensor units appropriately distributed around the region of interest. The sensing system includes or is associated with a control system. The latter is connectable to the sensor unit(s) for receiving and analyzing the response signal(s) and generating output signal indicative thereof.

The sensor elements containing compartments are arranged within the measurement unit in a spaced-apart relationship. This may for example be a circular array of sensor elements.

The sensing system also preferably includes a feeding unit for providing an input flow of a sample medium from the region of interest towards and through the measurement unit. Such a feeding unit may or may not be a constructional part of the sensor unit. In case of the circular array of the sensor elements' compartments, the sample medium is concurrently supplied to all the compartments. In case of a linear array, the sample medium is sequentially supplied to all the compartments.

The sample feeding unit is preferably configured as one or more suction assemblies. This may be one pump-like unit connected to an outlet of the measurement unit; or also another pump-like unit interconnected between the region of interest and an inlet of the measurement unit. In the latter case, the two pump-like units are operable in synchrony to provide a desired flow of the sample medium through the measurement unit.

The sample feeding unit may include a separate sample preparation unit connectable to the sensor unit; or an integrated sample preparation unit connectable to the measurement unit. The sample preparation unit may be configured as a separator for separating and filtering out a purified gas medium and collecting particles from the sample medium and directing a flow of the collected particles to the measurement unit. The sample preparation unit may include a pre-concentrate for collecting the sample medium, and a heating unit for heating the sample medium.

The sensing system may include a heating unit. The heating unit may be configured for heating the sample medium while flowing towards the measurement unit; and/or for heating inner surfaces of the sensor unit to prevent adsorption of the sample medium thereon.

The sensor unit may be configured as a two-part assembly to thereby enable operation of one sensor unit part during regeneration of the other.

The sensing system of the present invention may be configured for identifying one or more substances in a liquid medium, preferably in addition to the inspection of vapors in the vicinity of this liquid medium. To this end, the system includes a lift-like assembly for moving the measurement unit into and out of the liquid medium. The system may include two measurement units configured such that the first measurement unit is located outside the liquid medium during the system operation and is capable of identifying one or more foreign substances in vapors in the vicinity of the liquid medium, and the second measurement unit is driven for movement into and out of the liquid medium.

The measurement unit is preferably configured such that the compartments with the sensor elements are equally distanced from an actuator utility of a control system. The compartments may be arranged in a spaced-apart relationship along a circular path such that the actuator utility is located on a central axis of the circle, e.g., in the center of the compartments' plane.

Preferably, the sensor element is a piezoelectric crystal resonator characterized by a certain resonance frequency value and carrying reactive molecules of a kind capable of interacting with at least one specific foreign material to yield a reaction product that effects a change in the resonance frequency of the crystal resonator. This change is indicative of the identity of the at least one foreign material. The crystal resonator may be a quartz crystal. The piezoelectric crystal resonator is preferably configured as an inverted mesa structure having a membrane-like region. The membrane-like region is coated with metal electrodes on opposite sides thereof. Preferably, the crystal resonators of different sensor elements are modified with different reactive molecules, thereby enabling detection of various foreign materials. The control system is configured and operable for actuating the crystal resonators, measuring the change in the resonance frequency of the crystal resonators, and generating measured data indicative of the identity of foreign material(s).

The sensing system of the present invention may utilize a gate having side and top walls defining the region of interest inside the gate. Such a gate carries on its side and top walls a plurality of the sensor units such that the sensor units are exposed to air medium of the region of interest. Preferably, the gate on its side and top walls is formed with one or more air inlets for air blasting the region of interest and one or more air outlets for sucking in the air sample from the region of interest. The sensor units are mounted in the vicinity of the air outlets, respectively.

According to yet another broad aspect of the invention, there is provided a sensor unit for use in a sensing system for identifying at least one foreign material in a region of interest, the sensor unit comprising at least one measurement unit, the measurement unit comprising one or more sensor elements each configured and operable to be responsive to at least one foreign substance in the vicinity thereof, each sensor element being mounted in its own compartment having an inlet and an outlet thus defining an environmental region in the vicinity of the sensor element separated from the surroundings of the compartment.

According to yet another broad aspect of the invention, there is provided a sensor unit for use in a sensing system for identifying at least one foreign material in a liquid medium, the sensor unit comprising:

first and second measurement units, each comprising at least one sensor element, the sensor element being configured and operable to be responsive to at least one foreign material in its surroundings and generating a response signal indicative thereof, a drive assembly associated with one of the first and second measurement units for movement it into and out of the liquid medium, a sample feeding unit configured and operable for providing a flow of vapor from said liquid medium towards and through the other measurement unit.

According to yet another broad aspect of the invention, there is provided a gate unit having side and top walls defining a region inside the gate, the gate comprising in the side and top walls one or more air inlets for air blasting said region inside the gate and several air outlets for sucking in an air sample from said region, and comprising a plurality of sensor units mounted on the gate in the vicinity of said air outlets, respectively, each sensor unit being configured and operable to be responsive to at least one foreign material in its surroundings and generating a response signal indicative thereof.

According to yet another broad aspect of the invention, there is provided a method for use in identifying at least one foreign material in a region of interest, the method comprising: surrounding the region of interest by a predetermined number of spaced-apart sensor units, each sensor unit comprising at least one measurement unit configured and operable to be responsive to at least one foreign substance in its surroundings and to generate a response signal indicative thereof; providing a controllable air flow from region of interest towards and through the measurement units.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 10A shows data measured by the "gas medium" measurement unit and FIG. 10B shows data measured by the "liquid medium" measurement unit.

DETAILED DESCRIPTION OF EXEMPLARY EMBODIMENTS

A sensor system of the present invention can be used for detecting and analyzing various substances present in air vapor or liquid medium. The technique of the present invention can be used in a wide variety of commercial applications including, but not limited to, detection of explosives or drugs, environmental toxicology, biomedicine, such as microorganism classification or detection, material quality control, food and agricultural product monitoring, ambient air monitoring, employee protection, emissions control, and product quality testing.

The technique of the present invention could be used for substance detection in air vapor or liquid, thus acting as an electronic nose and/or as an electronic tongue. A combined device provides for simultaneous analysis of a solution and its vapors, providing a complete picture of the detected material.

Figure 1:
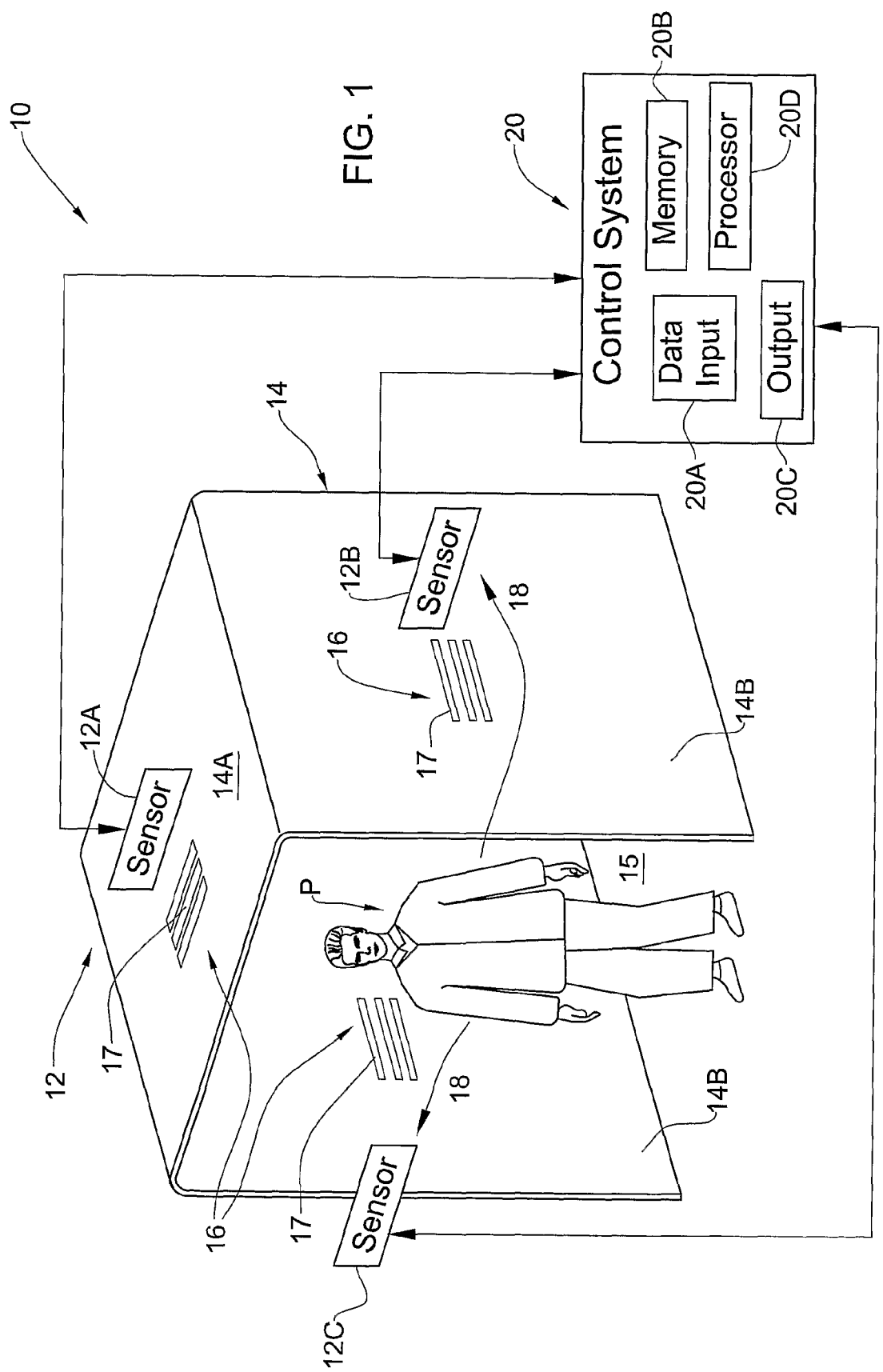
FIG. 1 is a: schematic illustration of a monitoring system of the present invention used for detecting substances that might be carried by a person.

Reference is made to FIG. 1 exemplifying a monitoring system 10 of the present invention used for identifying substance(s) of interest, for example explosives, that might be carried by a person. The system 10 includes a sensing assembly 12 accommodated in the vicinity of a person's path (constituting a region of interest). In the present example, sensing assembly 12 includes a plurality of chemical sensor units, three such sensor units 12A-12C being shown in the present example, arranged in a spaced-apart relationship around the person's path through a gate-like structure 14. The construction and operation of the sensor unit according to the invention will be described further below.

Gate-like structure 14 typically defines a top side 14A and side walls' assembly 14B around a region of interest (gate inside region) 15. Sensor units 12A-12C are arranged at different locations with respect to gate region 15, and accordingly with respect to a person P in the gate region. As shown in the present example, sensor unit 12A is associated with (i.e., is located on or in the vicinity of) top side 14A of gate 14, and sensor units 12B and 12C are associated with side walls' assembly 14B.

The inventors have found that the use of a plurality of sensor units arranged at different locations with respect to a region of interest (gate region in the present example) significantly improves the effectiveness of detection and reduces the time needed for effective detection. Preferably, each sensor unit is an assembly of two-parts ("doubled unit"). This enables to fasten the sensor unit preparation for the substance identification process: when one unit undergoes regeneration, the other unit performs substance identification.

As further shown in the figure, system 10 includes a sample input arrangement 16 for providing a flow of a sample medium (e.g., air sample) from region of interest 15 into the sensor units. In the present example, sample input arrangement 16 is associated with an appropriate number of air outlets made in gate 14, three such outlets 17 being shown in the present example associated with sensors units 12A-12C respectively. Sample input arrangement 16 is configured to suck an air sample 18 from gate region 15 into the respective sensor unit via air outlet 17. It should be noted, although not specifically shown, that the gate is also preferably provided with one or more air inlets for air blasting the region inside the gate.

Monitoring system 10 also includes a control system 20 which is configured to analyze data indicative of the measurement results coming from an appropriate utility of the sensor unit (as will be described below) and generate an output warning signal. The control system 20 is typically a computer system including inter alia a data input utility 20A, a memory utility 20B, a data processing and analyzing utility 20C, and a data output utility (e.g., display) 20D.

In the present example, control system 20 is shown as a stand alone system connectable (via wires or wireless) to the output of sensor units 12A-12C. It should, however, be understood that the present invention is not limited to this specific example, and alternatively, the control system may be formed by control units integrated within the respective sensor units. Output data of a specific sensor unit indicative of the existence of substance(s) of interest might be sufficient to identify the condition of the gate region (region of interest) as including the substance(s) of interest. The output warning signal may be a light or acoustic signal.

Figure 2A:
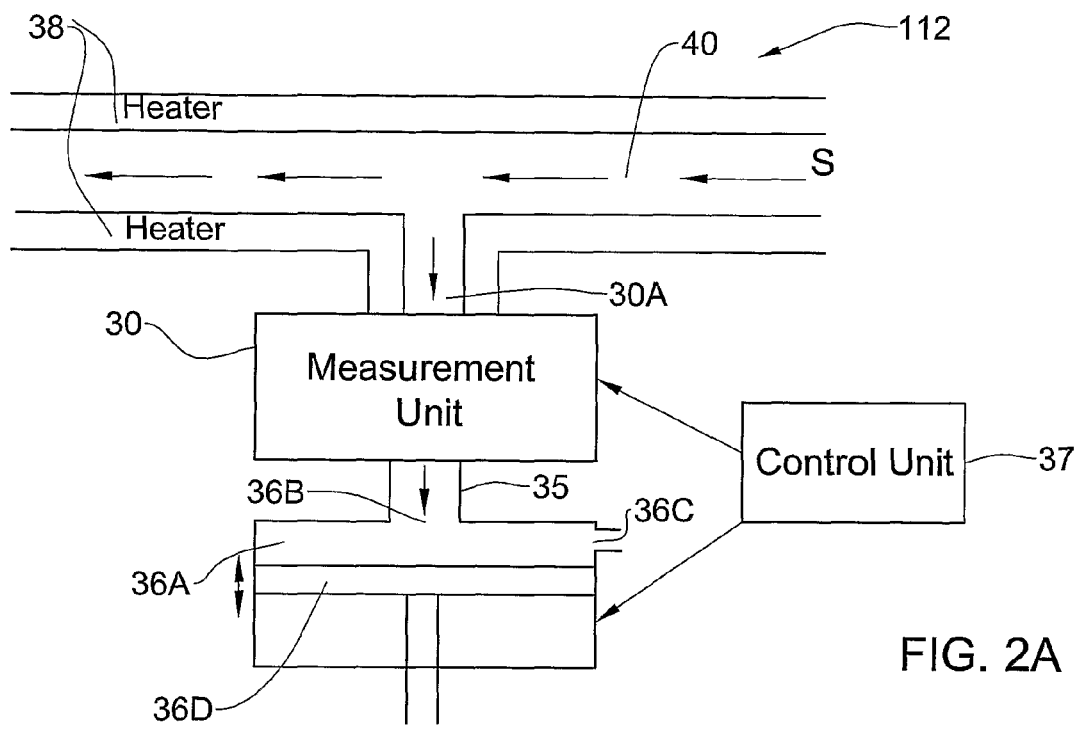
FIG. 2A shows an example of the configuration of a sensor unit of the present invention suitable to be used in system of FIG. 1.

Reference is made to FIG. 2A, schematically illustrating an example of a sensor unit 112 of the present invention suitable to be used in a monitoring system 10 (FIG. 1). Sensor unit 112 includes a measurement unit 30 including one or more sensor elements. According to the invention, each sensor element is preferably mounted in its own compartment having air flow inlet and output, and defines the environmental region in the vicinity of the sensor element separated from the surroundings of the compartment. Thus, in case an array of sensors is used, each sensor is in its own compartment, separated from other compartment(s) containing other sensor element(s) respectively, as will be described further below with reference to FIG. 3. The sensor element is configured and operable to be responsive to at least one foreign material in its surroundings and generate a response signal indicative thereof.

Preferably, sensor unit 112 also includes a heating unit 38 (one or more heater elements) configured for heating the sample prior to entering measurement unit 30. In the present example, sample S is heated while flowing towards measurement unit 30. To this end, sensor unit 112 defines a transport path 40 towards the measurement unit, and the heating unit is associated with this path, e.g., extends along this path. This may be implemented by providing a tube 40 (e.g., of about 5 mm diameter) along which a direct continuous flow of an air-vapor sample S is provided from outside towards measurement unit 30. Two spaced-part heater elements 38 (or spaced-apart arrays of heater elements) are accommodated at opposite sides of tube 40. Tube 40 is connected to an inlet 30A of measurement unit.

It should be noted, although not shown here, that preferably the sample is previously prepared (e.g., by separation of particles from air and heating the sample, as will be exemplified further below) in a separate sample preparation unit.

Further provided in sensor unit 112 is a suction unit 36 accommodated adjacent to measurement unit 30 and connected thereto through an appropriate tube-like connector 35. Unit 36 is a pump-like assembly having a chamber 36A with an inlet 36B connectable to tube 35 and thus to measurement unit 30, an outlet 36C, and a piston 36D. The latter is operable by a control unit 37 to provide a desired flow of sample S through measurement unit 30. Thus, section unit 36 serves for passing the sample flow through measurement unit 30. Suction unit 36 may also serve for feeding clean air or inert gas into measurement unit 30 for cleaning the system and preparing it for further measurements.

It should be noted that an appropriate number of sensor units (or doubled units as the case may be) varies with the device application. For example, for the application exemplified in FIG. 1, namely for detection and identification of explosives that might be carried by a passenger (e.g., in airport), seven sensor units might be used, three sensor units at each side wall and one sensor unit at the top wall of the gate. Preferably, each unit is a two-part unit, as described above, thus the total number of sensor units associated with the gate being 14.

The technique of the present invention provides for a very short detection time. The detection time, including time required for suction of an air sample and its preparation for feeding to sensors containing compartments (described further below), for the chemical analysis, and for the data processing and outputting the results, can practically be of about 12 seconds or less, where the time period for the chemical analysis, data processing and outputting the results is about 1-2 seconds.

Figure 2B:
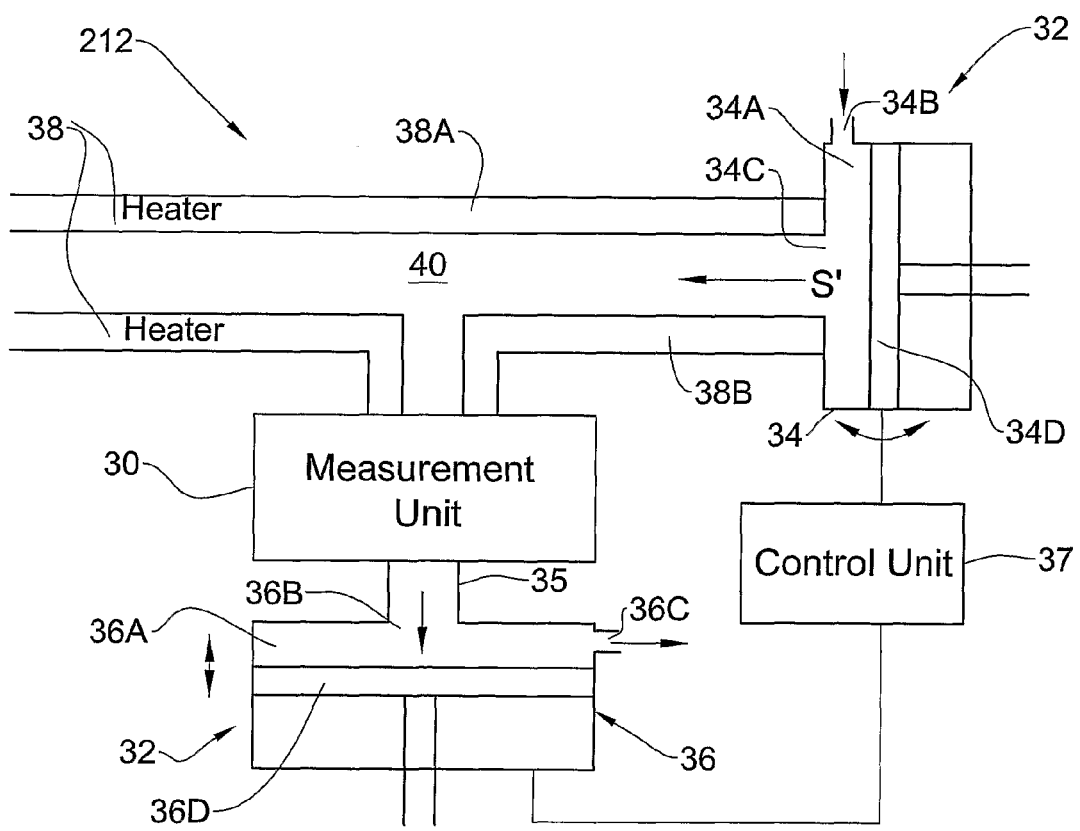
FIG. 2B schematically illustrates another example of a sensor unit of the present invention.

Referring to FIG. 2B, there is schematically illustrated another example of a sensor unit 212 of the present invention. In the present example of FIG. 2B, sensor unit 212 is configured for inspecting an air-vapor sample.

Figure 7:
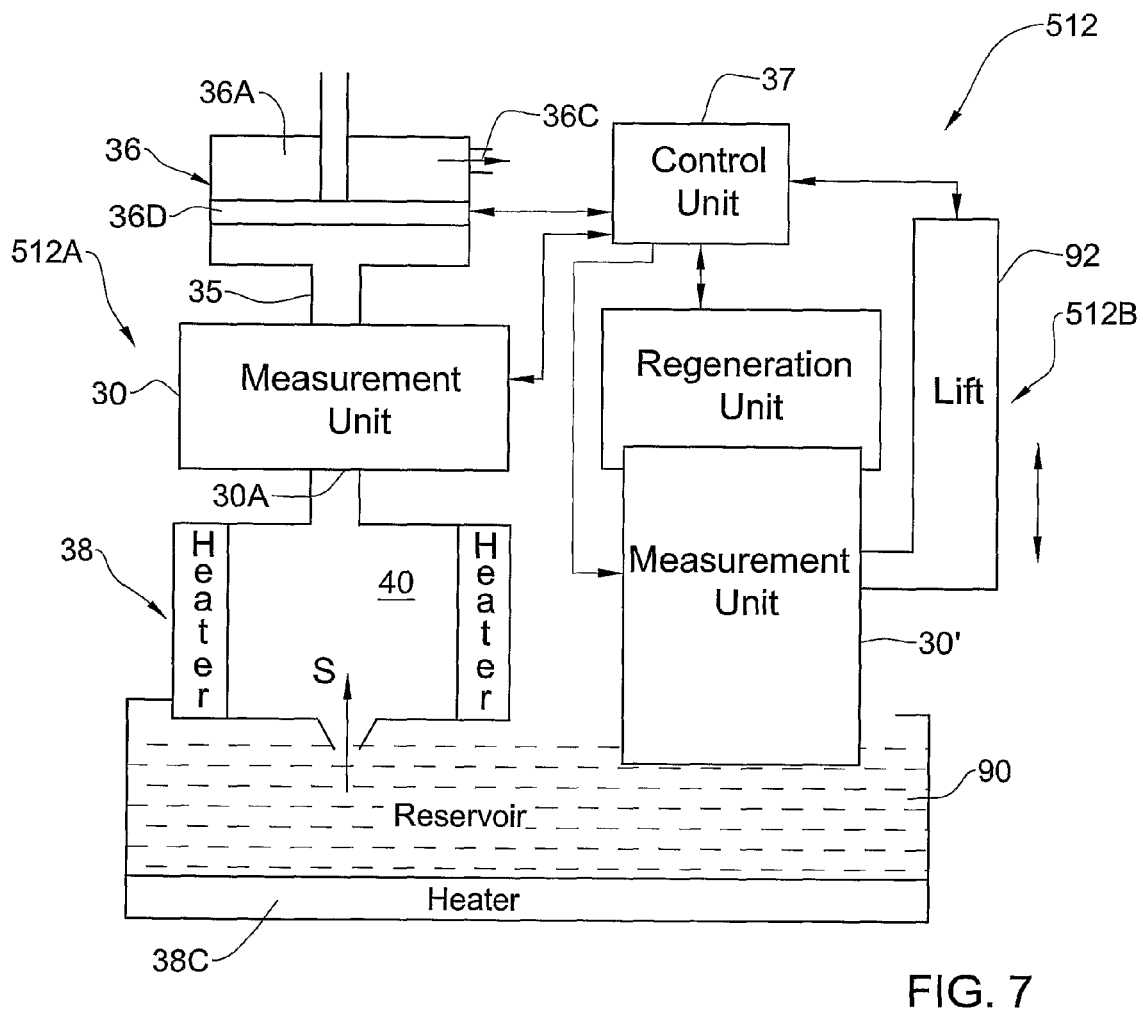
FIG. 7 exemplifies another configuration of a sensor unit of the present invention configured for inspecting liquid samples.

It should be noted that a sensor unit of the present invention may also be configured for detecting foreign substance(s) in a liquid medium, which will be exemplified further below with reference to FIG. 7.

Sensor unit 212 includes a measurement unit 30 and a sample feeding unit 32 for passing the sample flow through the measurement unit. Measurement unit 30 is configured as described above namely includes sensor elements each mounted in its own compartment separated from other compartment(s) containing other sensor element(s) respectively.

Sample feeding unit 32 includes an input unit 34 and an output unit 36 at opposite sides of measurement unit 30. Input unit 34 is either connectable to an external sample input arrangement in the vicinity of a region of interest, or as shown in the present example is configured as the sample input arrangement for providing a flow of a sample medium towards measurement unit 30.

Input unit 34 presents a pump-like assembly having a chamber 34A with an inlet 34B exposed to the region of interest, an outlet 34C, and a movable piston 34D driven by a control unit 37. It should be understood that control unit 37 may or may not be part of the control system (10 in FIG. 1) associated with the sensor output signals. Output unit 36 is a similar pump-like assembly having a chamber 36A with an inlet 36B connectable via an appropriate tube-like connector 35 to measurement unit 30, an outlet 36C, and a piston 36D. Piston 36D is operable by control unit 37 synchrony with piston 34D, to provide a desired flow of a sample S through measurement unit 30. Pistons 34D and 36D operate in opposite operational modes: when piston 34D presses the sample out of chamber 34A towards measurement unit 30, piston 36D sucks this sample into measurement unit 30. Output unit 36 may also serve for feeding clean air or inert gas into measurement unit 30 for cleaning the system and preparing it for further measurements.

Preferably, sensor unit 212 also includes a heating unit 38, which in the present example is configured and accommodated similar to the above-described example of FIG. 2A, namely associated with the sample flow path from the input unit towards the measurement unit. It should be noted, although not specifically shown here, that heating unit 38 may include additional heating element(s) associated with input unit 34, namely accommodated for heating the air sample while in the input unit.

Thus, inlet 34A of input unit 34 is connectable to the region of interest (e.g., to air outlet 17 in gate 14 in FIG. 1), and outlet 34B is connectable to the sample transport path 40 (or directly to measurement unit 30 as the case may be).

For example, the sample is heated to 140-200° C. The heating temperature is defined by the evaporation temperature of foreign material(s) to be detected. The vapor flow towards and through the measurement unit is defined by the operation of input and output pump-like assemblies 34 and 36. For example, the air vapor flow of 0.5 m/sec rate through the sensor element compartment provides the sensor element response time of about 1 sec.

Figure 3:
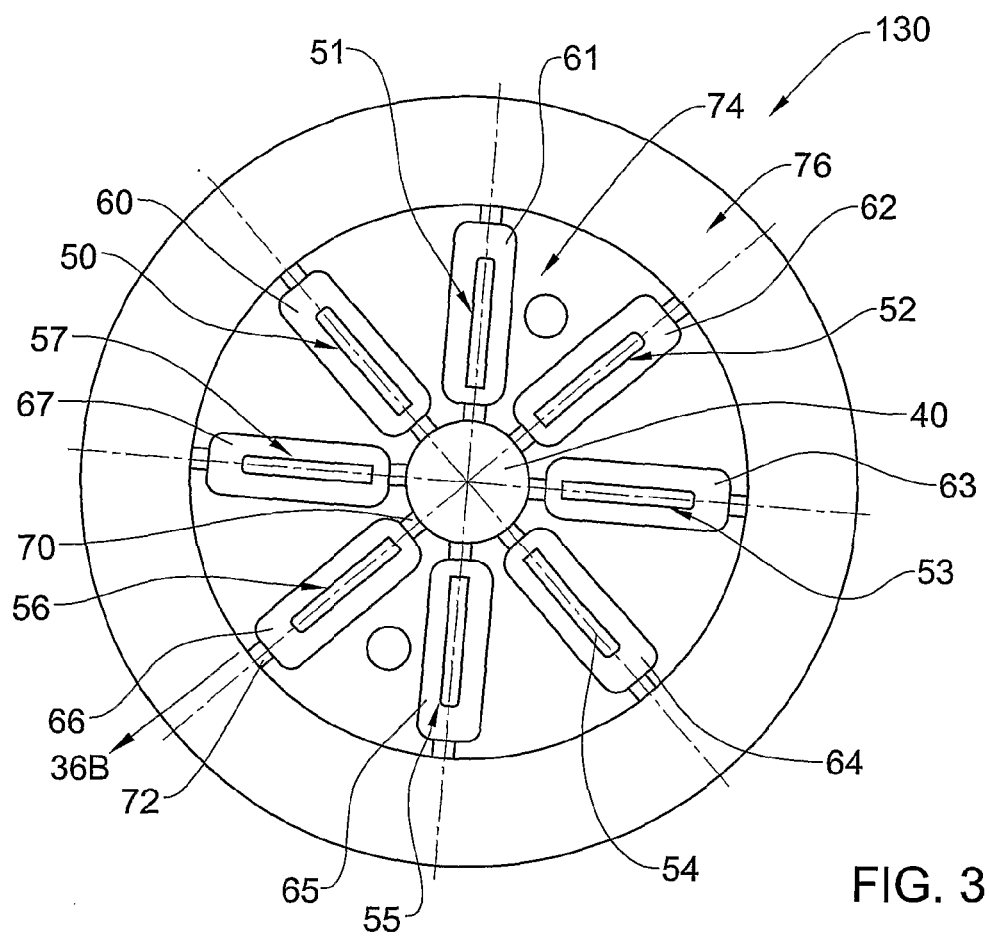
FIG. 3 shows an example of a measurement unit of the present invention for use in the sensor unit.

Reference is made to FIG. 3 illustrating an example of a measurement unit 130 according to the invention suitable to be used in the sensor unit. Measurement unit 130 includes an array of sensor elements (piezoelectric crystal resonators), eight such elements 50-57 being shown in the present example arranged in a circular array with equal spacings between the elements. Sensor elements 50-57 are mounted in compartments 60-67, respectively. Compartments with sensor elements are mounted on a measurement matrix 74. The latter is configured as a chamber appropriately shaped (e.g., cylinder) to ensure substantially uniform distribution of evaporated and transported sample among all the sensor elements. Matrix 74 is mounted on a support structure 76 presenting a cavity into which the compartments can be opened.

Each compartment has an inlet opening, generally at 70, and an outlet opening, generally at 72, for the sample flow through the compartment. During the system operation, the sample enters the compartment through inlet 70 and emerges therefrom through outlet 72. During the system regeneration, these inlet and output openings serve for the flow of a clean gas (air or inert agent) through the compartment. The dimensions and shape of the compartment, as well as those of inlet and outlet openings and the cavity 76, are selected so as to meet the aerodynamic requirements, consisting of providing natural oscillations of piezo-sensors on the one hand, and a desired speed of the sample free flow on the other hand.

Thus, each sensor element is accommodated in its own compartment separated from those of other sensor elements. The air flow carrying the sample to be inspected is equal for all the sensors. The amount, speed and pressure of this flow are controlled. In this case, unavoidable noise is reduced to minimal (a few tens of Hertz at the crystal vibration frequency of 250 MHz). Such a configuration of the measurement unit provides for a significant increase in the possibility of substance detection, increase in adsorption processes, which leads to a practically immediate substance identification (in about 1 second).

In order to provide homogeneous flow of the sample towards all the sensor elements, the sensor elements may be arranged in a linear array such that the sample is sequentially supplied to the sensor elements (e.g., the 60 mm length chamber of the measurement unit including an array of 8 sensor elements), or may be arranged in a circular array as shown in FIG. 3 in which case the sample is concurrently supplied to all the sensors.

Preferably, the piezoelectric crystal resonator is configured as an inverted mesa structure having a membrane-like region and being characterized by a certain resonance frequency value (e.g., 0.1-1.2 GHz), the crystal resonator being excitable by the environment to cause a change in the resonance frequency thereof from this certain resonance frequency value. This technique is described in U.S. Pat. No. 6,526,828, assigned to the assignee of the present application.

Figure 4:
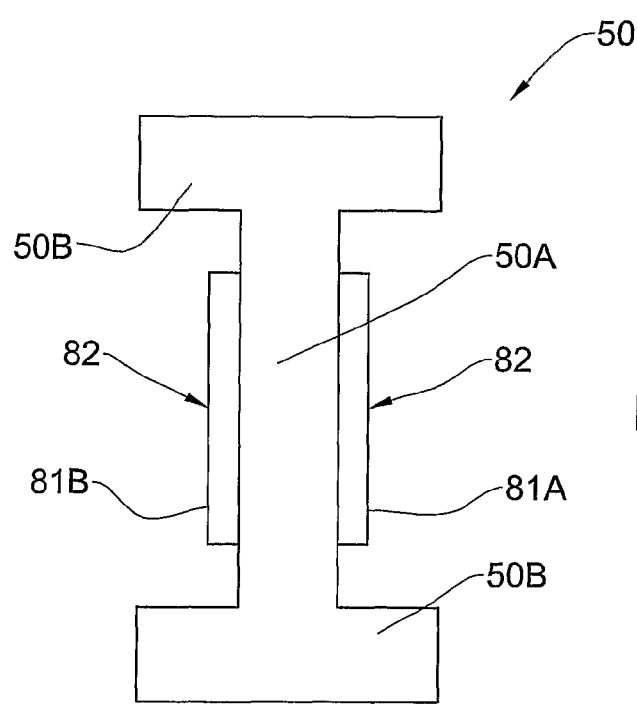
FIG. 4 exemplifies a preferred configuration of a sensor element suitable to be used in the measurement unit of the present invention.

This is illustrated in FIG. 4, showing sensing element 50, which is a quartz crystal resonators in the form of an inverted mesa structure defining a membrane-like region 50A having a thickness of about several micrometers, between thicker end regions 50B of the crystal. To fabricate such an inverted mesa structure, a crystal is patterned either at one side thereof to form one recess, or at both opposite sides thereof (as shown in the present example) to form two opposite recesses, thereby forming membrane central region 50A of a sufficiently small thickness (to obtain desirably high sensitivity of the sensor). Metal electrodes 81A and 81B (made from Al, Pt or Au) are deposited onto opposite surfaces of membrane-like region 50A. Quartz crystal resonator 50 is formed with a surface region 82 (exposed to the environment) modified by reacting molecules intended to interact with one or more specific foreign materials that may be present in the environment. In the present example, this is implemented by coating electrodes 81A and 81B with such a molecule. Generally, such a modified surface region may include the surface of the electrodes (or only one electrode located on that side of the device by which it is exposed to environment), the surface of the membrane-like region, or both. An interaction between these molecules and one or more specific foreign material affects the frequency of vibration of the crystal resonator to change it from the certain resonance frequency value. This change is detected by the corresponding utility of the control system. The principle of the detection is that the frequency of vibration of an oscillating crystal is decreased by the absorption of a foreign material on its surface. A foreign material is selectively absorbed by the coating (on the crystal surface or/and on the metal electrode surface coating the crystal surface), thereby increasing the weight of the crystal and decreasing the frequency of vibration.

What is actually detected by the sensor unit utilizing several crystal resonators is the so-called "electronic image" or pattern of the intensities of response of each of the crystal resonators. These responses are indicative of diminution of the vibrating frequencies of the crystal resonators caused by the absorption of foreign materials.

The modification of the surface region of the crystal resonator may be achieved by two alternative techniques: (1) construction of organized, self assembled monolayers (SAM); or (2) formation of polymeric layer. SAM consists of receptor compounds comprising a linker that connects this compound to the surface of a substrate, an optional spacer, a structural element and an active head group. Relating to the formation of a polymeric layer, the preferred technology for forming a polymer layer in a controlled manner is by electropolymerization.

Figure 5:
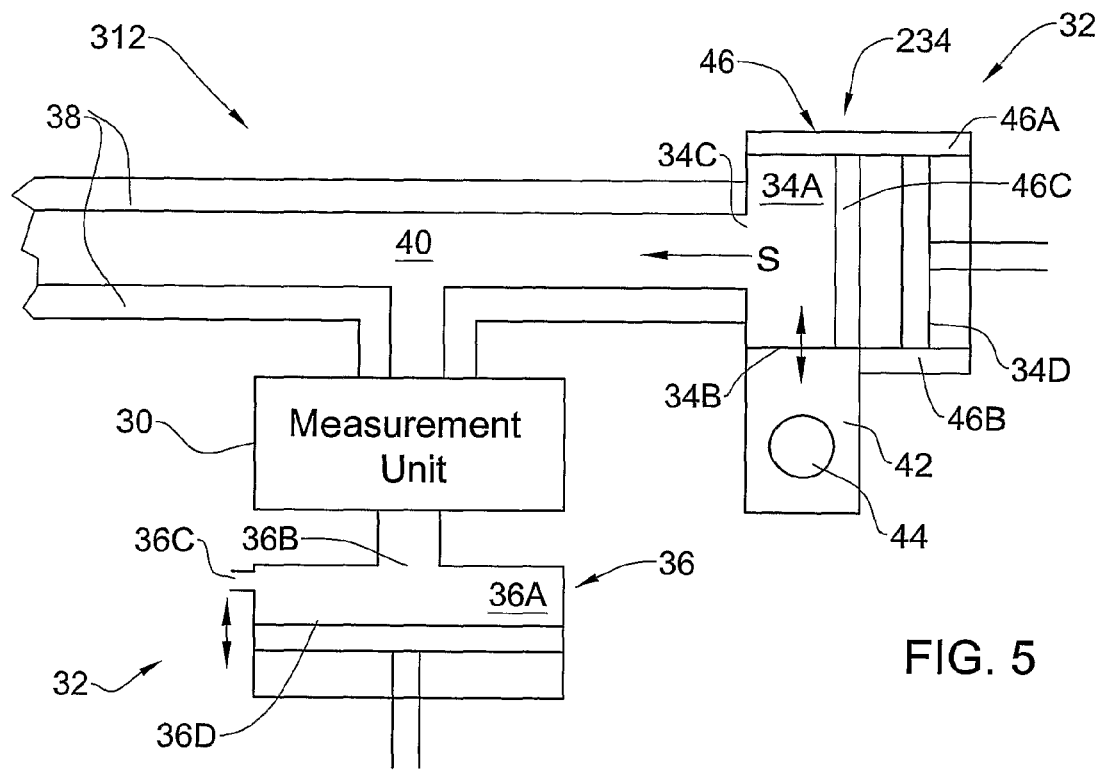
FIGS. 5 and 6 show two more examples, respectively, of a sensor unit of the present invention.

FIG. 5 illustrates yet another example of a sensor unit 312 of the present invention for inspecting an air-vapor medium sample for foreign substance(s). Sensor unit 312 is configured as a portable table-type device. To facilitate understanding, the same reference numbers are used for identifying components that are common in all the examples of the invention.

Sensor unit 312 includes a measurement unit 30 and a suction assembly 32. Measurement unit 30 is configured generally as described above, and namely includes an array (e.g., circular array) of crystal resonators, each in its own compartment separated from other sensor element(s), preferably with the resonator configuration as a mesa structure. Suction assembly 32 includes an input unit 234 having a pump-like assembly formed by a chamber 34A with inlet 34B and outlet 34C and a driven piston 34D, and an output unit 36 configured as a similar pump-like assembly formed by a chamber 36A with inlet 36B and outlet 36C and a driven piston 36D. Input and output pump-like assemblies (their pistons 34D and 36D) are synchrony operated as described above to provide a desired flow of a sample medium S through measurement unit 30.

In the present example of FIG. 5, input assembly 234 also includes a sample preparation unit 42 configured for accommodating a pre-concentrate 44. The latter is configured as a mesh of an array of small cells, for example made of stainless steel, kept under tension between two metal rings (a tambour-like assembly). Such a pre-concentrate assembly 44 is appropriately insertable into chamber 42. Further provided in sensor unit 312 is an additional heating unit 46, which in the present example is in the form of two spaced-apart heaters (or two arrays of heaters) 46A and 46B at opposite sides of chamber 34A so as to be at opposite sides of the sample flow from chamber 34A towards a sample flow path 40 and also optionally an internal heater 46C inside chamber 34A. Sample S is thus appropriately heated, and a resulting vapor flows towards measurement unit 30.

Thus, the sample may be supplied into the measurement unit in one of the following ways: using heating a special pre-concentrate, which provides evaporation and flow of vapor of the material collected on the pre-concentrate; by depositing a certain amount of a sample material onto the pre-concentrate with no heating; or by direct suction of a sample media and flowing it to and through the measurement unit. To prevent adsorption of the sample media on the inner walls of the input chamber as well as on the piston of the input unit, these walls and piston as well as other inner surfaces of the input unit, where collection and momentary storage of the sample might occur, could be heated up to a temperature sufficient to avoid the adsorption. Similarly, all the system parts through which the sample media is supplied to the measurement unit, could be appropriately heated. The use of additional internal heater 46C (e.g., IR laser) provides for accelerating the entire detection process.

Figure 6:
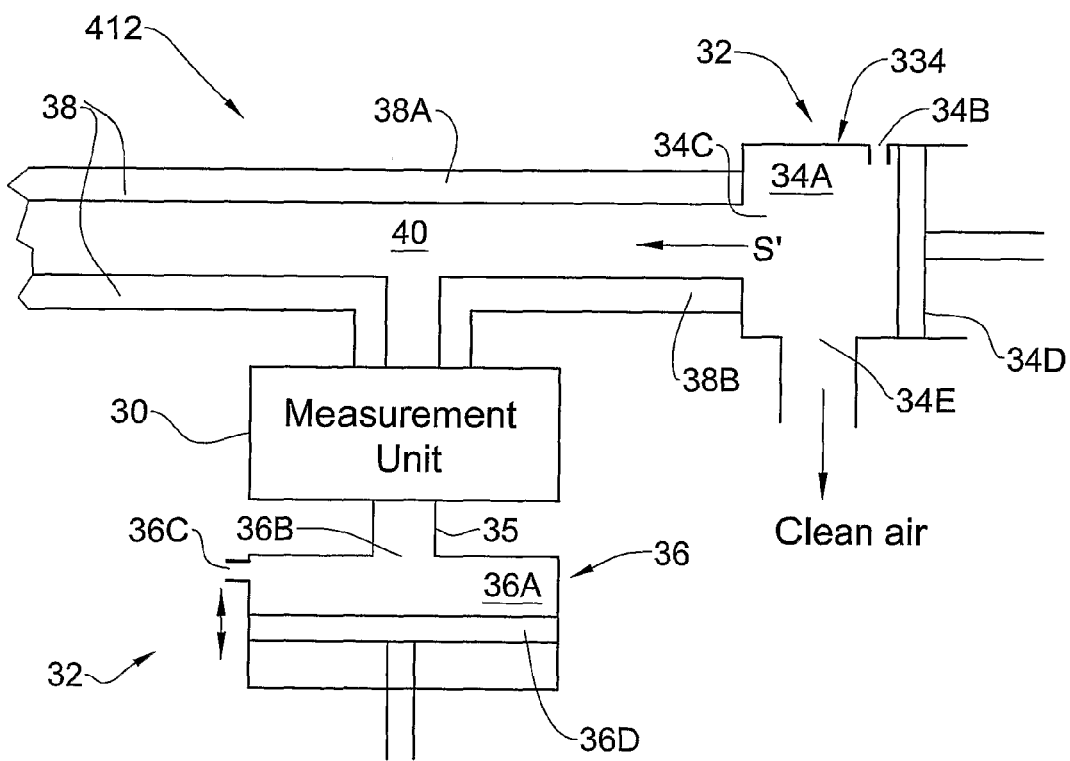

FIG. 6 shows yet another example of a sensor unit 412 of the present invention. Sensor unit 412 includes a measurement unit 30 and a suction assembly 32. Measurement unit 30 is preferably configured as described above, namely includes an array (e.g., circular array) of crystal resonators (preferably in the form of mesa structures), each in its own compartment separated from other sensor element(s). Suction assembly 32 includes an input unit 334 and an output unit 36 at opposite sides of measurement unit 30. Preferably, sensor unit 412 also includes a heating unit 38 associated with a sample flow path 40 from input unit 334 to measurement unit 30.

In the present example, input unit 334 is a separate unit connectable to an inlet of measurement unit 30 or to inlet of path 40, and is configured as a separator assembly formed by a single separator or an array of separators arranged in a cascade-like manner. Such a separator may for example include a cyclone-like assembly configured for the purposes of the present invention for filtering out, via outlet 34E, a part of the sample purified from dust and other particles, while collecting the remaining part (particles) of the sample and directing it into measurement unit 30 via outlet 34C. The collected part of the sample medium is preferably heated (e.g., to 140-200° C.) by heating unit 38 prior to entering measurement unit.

The system of the present invention operates as follows: A sample of media from a region of interest is input into the sensor unit. The sample may be directly flowed from the region of interest to and through the measurement unit (a matrix carrying a plurality of sensors) as exemplified in FIGS. 2A-2B and 6, or may be first collected and prepared (using a pre-concentrate with or without heating) and then flowed to the measurement unit as exemplified in FIG. 5.

As indicated above, the sensor unit of the present invention may be configured for detecting foreign substance(s) in a liquid medium as well. This is illustrated in FIG. 7. A sensor unit 512 is configured as a portable table-type device, and is formed by two concurrently operating parts 512A and 512B both associated with a reservoir 90 containing a liquid to be inspected. One part 512A of the sensor unit is configured for inspecting an air-vapor sample for one or more foreign substances, and includes a first measurement unit 30 (to be located outside the liquid medium during the device operation) and a suction unit 36, and preferably also includes a heating unit 38, for example in the form of an annular-shape element (all configured and operable as described above with reference to FIG. 2A). The other part 512B of the sensor unit is configured and operable to examine a liquid sample, and includes a second measurement unit 30' which is configured similar to the first measurement unit 30 and is driven to be dipped into the liquid at a predetermined depth during the device operation. The second measurement unit is associated with a regeneration unit 92 such that when this measurement unit is moved out of the liquid medium, the sensor elements' matrix undergoes regeneration. Each sensor element of unit 30' is to be completely dipped into the liquid. In order to smoothly dip the sensors into liquid at a predetermined depth, a micro-lift assembly 92 is provided being appropriately operated by a control unit 37. Preferably, an additional heater 38C is provided for heating the liquid in reservoir 90. Each of the measurement units 30 and 30' includes a single sensor element, preferably mounted in a compartment; or an array of two or more sensor element, for example arranged as described above (i.e., each in its own compartment).

Figure 8:
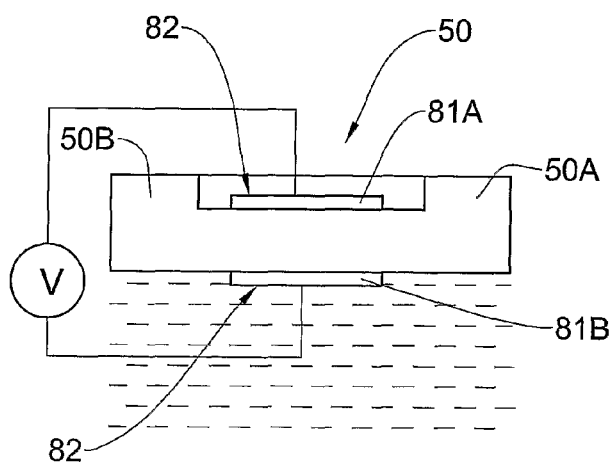
FIG. 8 exemplifies the configuration of a sensor element suitable to be used in the sensor unit of FIG. 7.

FIG. 8 exemplifies the configuration of a sensor element 50 of measurement unit 30'. As shown, the sensor element is configured such that, when being dipped into liquid, only one side thereof is exposed to liquid while the other side is sealed.

To actuate oscillations of the crystal resonators (sensor elements) of measurement units 30 and 30', appropriate electric signals are applied. With regard to measurement unit 30', the power supply should be such as to ensure that the crystal resonator's oscillations could overcome the oscillations of liquid medium. Electrical signals providing activation of the crystal resonators are created by a specifically design electron circuit operating as the so-called "electronic oscillator" or "amplifier". The construction and operation of such an electronic circuit do not form part of the present invention and therefore need not be specifically described. For example, a symmetric electronic circuit, disclosed in the above-indicated U.S. Pat. No. 6,526,828 assigned to the assignee of the present application, can be used. Sensors used in the air-medium related measurement unit may for example operate with about 250 MHz frequency of oscillations, as described in U.S. Pat. No. 6,526,828. The liquid-medium related measurement unit may operate with about 30 MHz frequency.

When sensor element(s) of unit 30' is/are dipped into liquid, the sensor element(s), coated with appropriate adsorbent(s), can adsorb specific substance(s) present in the liquid. In this case, the frequency of oscillation of the sensor element(s) is changed in accordance with concentration of the specific substance(s), and in case of a plurality of such elements in accordance with the selectivity of the coating on the sensor elements. When the adsorbed substances are analyzed, measurement unit 30' is lifted up, and the matrix of sensor elements is dried (flowed by clean and warm air). Thus, sensor unit provides for concurrently analyzing vapors and substances in a liquid medium.

The following are experimental results for the technique of the present invention.

Figure 9A:
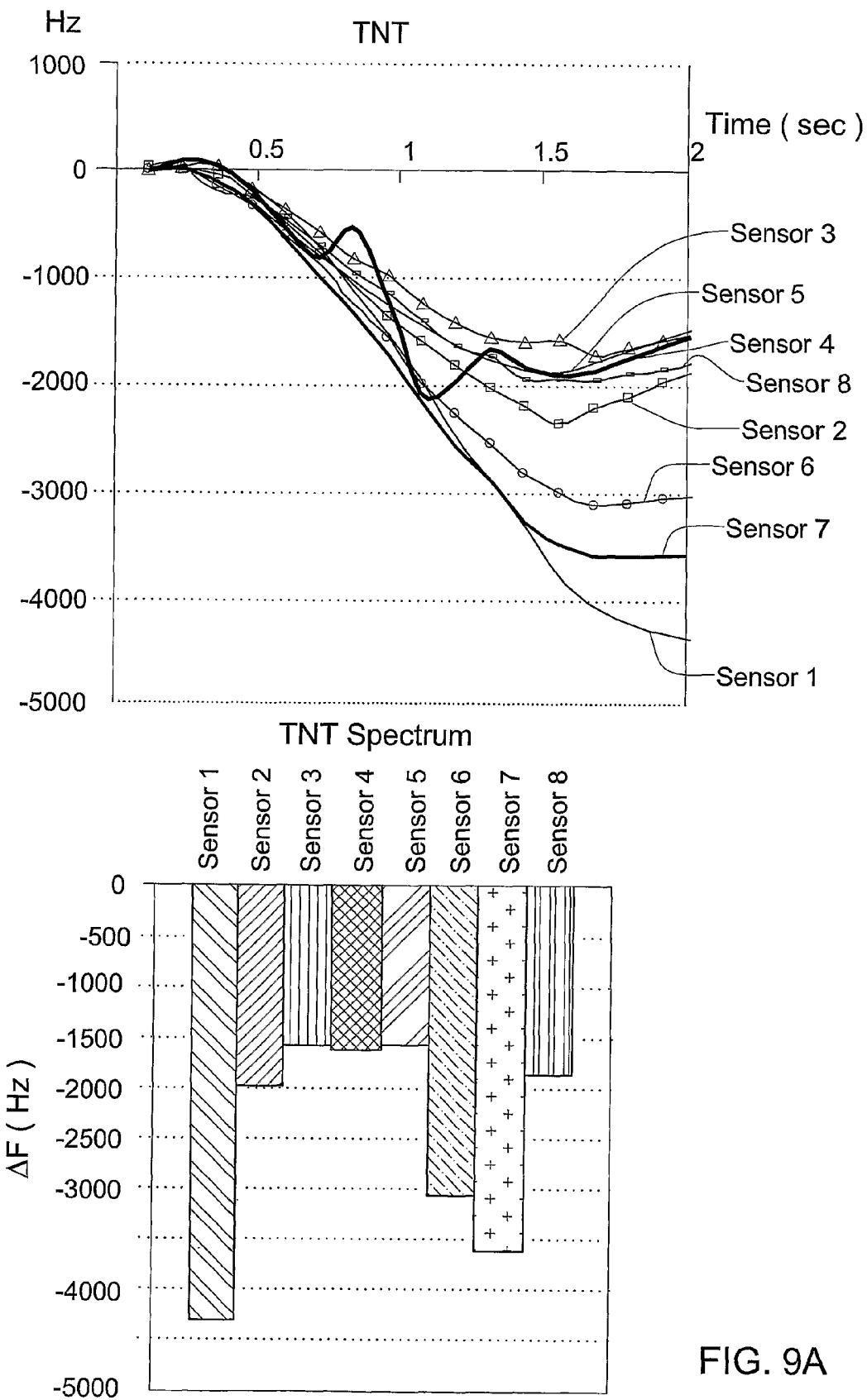
FIGS. 9A-9C show the experimental results of using the sensing unit of the present invention for identifying different foreign substances.
Figure 9B:
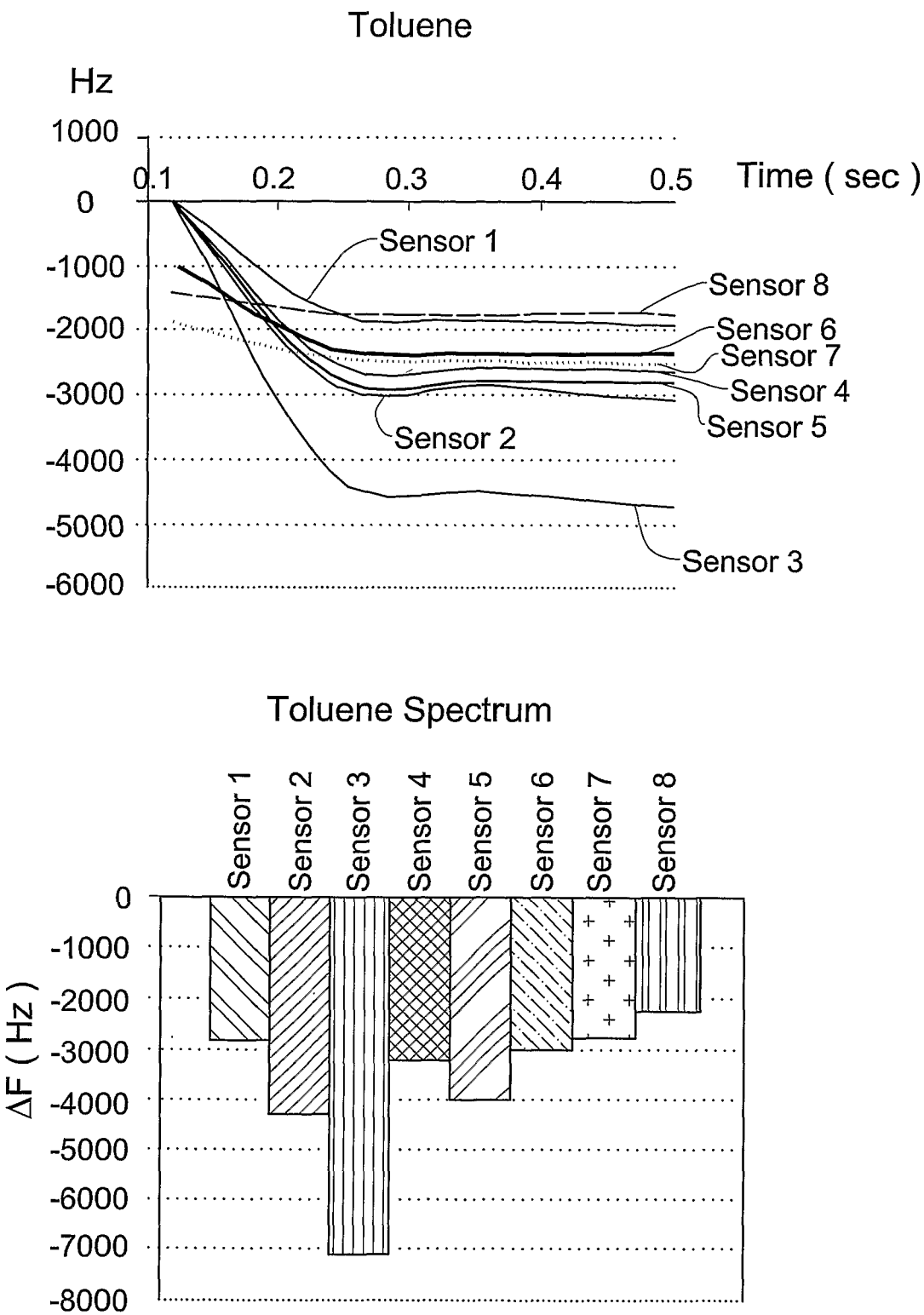
Figure 9C:
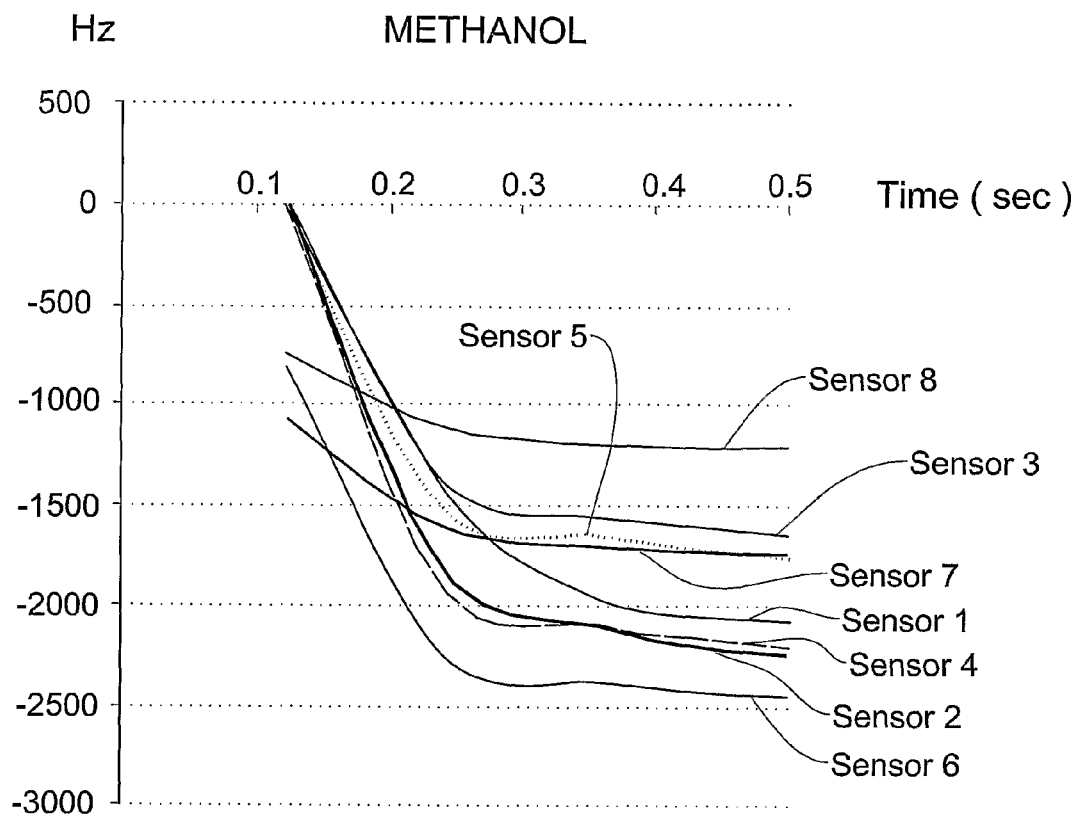
Figure 9C:
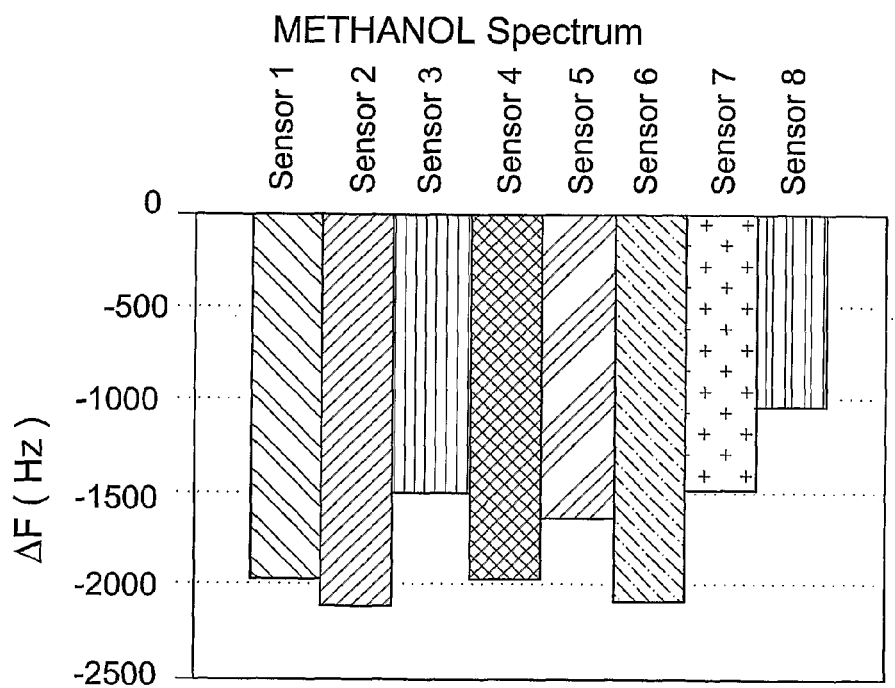

Reference is made to FIGS. 9A-9C showing the experimental results of using the sensor unit of the present invention for identifying various foreign substances in an air sample, namely TNT (explosives), Toluene and Methanol (volatile substances). In the present example a sensor unit formed by a circular array of eight sensor elements was used (each sensor element in its own separate compartment). As shown for example, for TNT (FIG. 9A), a time period of 2 seconds is sufficient for the detection of a certain substance, while in the 1.5-2 sec time period the order of the sensor elements order is determined in accordance with the adsorption level defined by a selective coating on the sensor element surface. This is more clearly illustrated in the spectral graph. The amplitude of response of each sensor element, relative to the other sensor elements presents a stable sequence, which is weakly dependent on the amount of substance and the temperature conditions. This sensors' sequence, termed "finger print" or "image" of the substance, showed the repetition close to 10%.

Figure 10A:
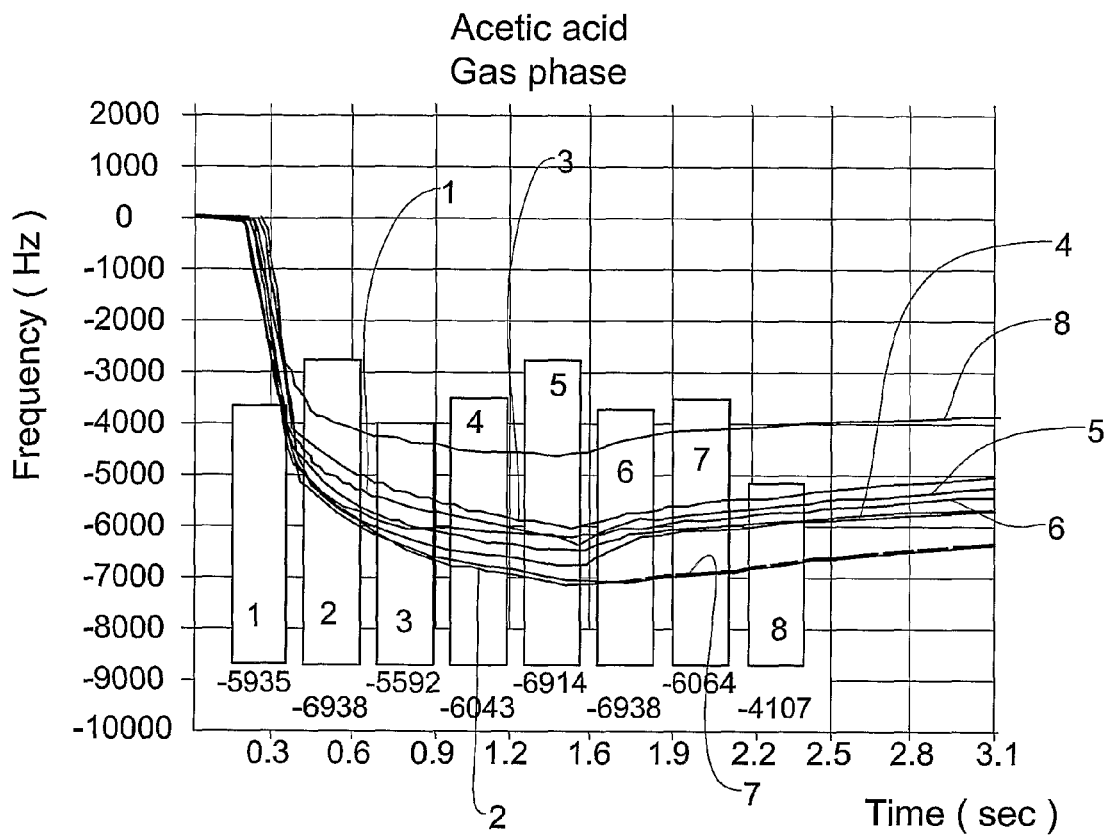
FIGS. 10A and 10B illustrate the experimental results of using the sensor unit of FIG. 7 for identifying acetic acid in a liquid sample, where
Figure 10B:
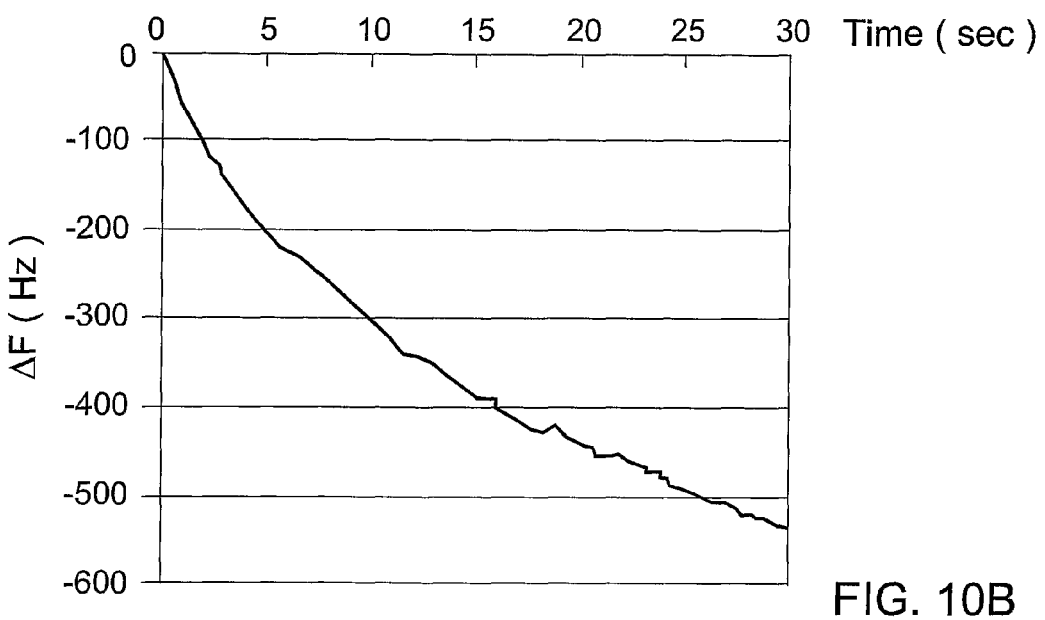

FIGS. 10A and 10B illustrate the experimental results of using the sensor unit of the present invention for identifying acetic acid in a liquid sample. FIG. 10A shows data measured by the "gas medium" measurement unit (30 in FIG. 7). This measured data is in the form of time variations of the crystal resonators' oscillations (eight resonators in the present example) and the spectral representation of the same. FIG. 10B shows data measured by the "liquid medium" measurement unit (30' in FIG. 7). In the present example, measurement unit 30 was built from a circular array of sensor elements and unit 30' from a single sensor element, but is should be understood that the present invention is not limited to this specific example.

Figure 11A:
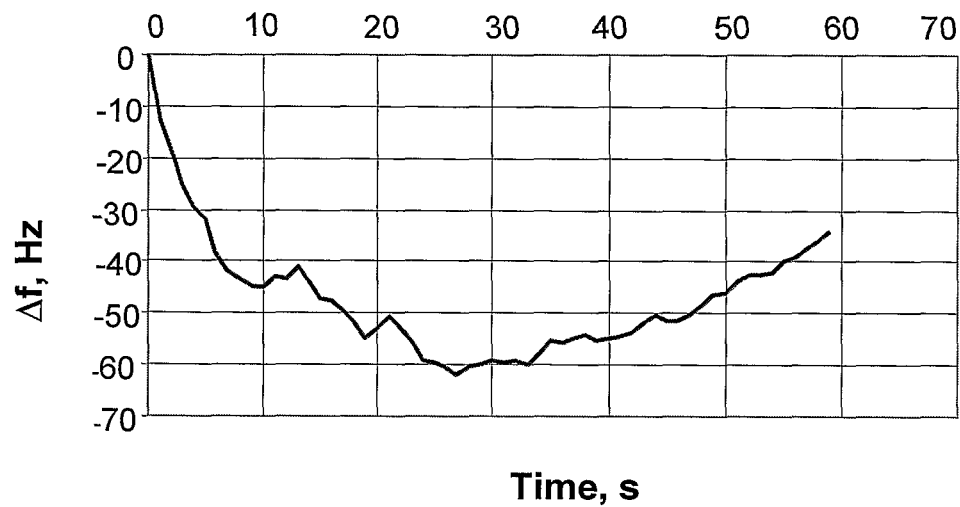
FIGS. 11A and 11B illustrate the experimental results of using the sensor unit of FIG. 7 for identifying urine vapor above liquid level, using 150 MHz and MHz measurement modes, respectively.
Figure 11B:
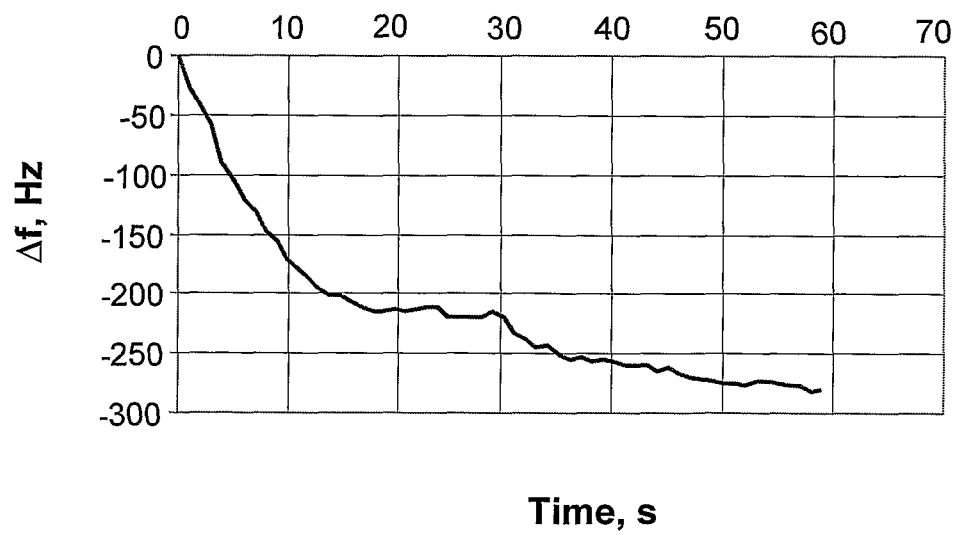

FIGS. 11A and 11B illustrate the experimental results of using the sensor unit of the present invention for identifying urine vapor above liquid level. FIG. 11A shows data measured by the 150 MHz measurement unit 30 (FIG. 7). FIG. 11B shows data measured by the 30 MHz measurement unit 30. In the present example, measurement unit 30' was built from a circular array of sensor elements, but is should be understood that the present invention is not limited to this specific example.

Thus, the present invention provides a simple and effective monitoring system for detecting various foreign materials in the vicinity of a sensor unit. Accommodation of the sensor element in a separate compartment significantly improves the substance identification and makes it very quick. The use of a suction assembly provides for controlling the speed, temperature and pressure of the sample flow to and through the measurement unit. The separation between the measurement unit and the sample preparation unit (as exemplified in FIG. 5) allows for eliminating or at least significantly reducing the affect of the sensor element accommodation in space (in the gravity field) on the sample-carrying flow in the measurement unit.

Those skilled in the art will readily appreciate that various modifications and changes can be applied to the embodiments of the invention hereinbefore exemplified without departing from its scope defined in and by the appended claims.

The invention claimed is:

1. A sensing system for use in identifying at least one foreign substance in a region of interest, the sensing system comprising a certain number of sensor units, each sensor unit comprising;

at least one measurement unit, and a sample flow path for flowing a sample medium towards an inlet of the measurement unit the sample flow path comprising at least one heating unit for heating the flowing sample medium prior to entering the measurement unit through said inlet, said at least one measurement unit comprising a plurality of sensor elements each configured and operable to be responsive to at least one predetermined foreign substance in the vicinity thereof and to generate a response signal indicative thereof, each of the sensor elements being mounted in its own compartment having an inlet and an outlet thus defining an environmental region in the vicinity of said sensor element separated from the surroundings of the compartment and from other compartments in said measurement unit, thereby increasing concentration of the sample medium in the vicinity of each of the sensor elements, wherein the compartments with the sensor elements are arranged in a spaced-apart relationship with respect to one another and said inlet of the measurement unit and are mounted on a measurement matrix configured to ensure substantially uniform distribution of the heated sample medium among all the compartments.

2. The sensing system of claim 1, comprising at least two sensor units.

3. The system of claim 1, comprising a control system connectable to the sensor unit for receiving and analyzing the response signal and generating output signal indicative thereof.

4. The system of claim 3, wherein the compartments with the sensor elements are equally distanced from an actuator utility of the control system.

5. The system of claim 4, wherein the compartments are arranged in a spaced-apart relationship along a circular path, the actuator utility being located on a central axis of the circle.

6. The system of claim 5, comprising a disc formed with a circular array of the compartments with the sensor elements, the control system comprising an actuator utility located in the center of the disc.

7. The system of claim 1, wherein the compartments are arranged within the measurement unit in a spaced-apart relationship along a predetermined path.

8. The system of claim 1, wherein the compartments are arranged within the measurement unit in a spaced-apart relationship along a circular path.

9. The system of claim 1, comprising a feeding unit configured and operable for providing an input flow of a sample medium from the region of interest towards and through the sample flow path, and the heating and measurement units.

10. The system of claim 9, wherein the compartments are arranged within the measurement unit in a spaced-apart relationship along a circular path, the sample medium being concurrently supplied to all the compartments.

11. The system of claim 9, wherein the compartments are arranged in a one-dimensional array, the sample medium being sequentially supplied to all the compartments.

12. The system of claim 9, wherein the sample feeding unit comprises a suction assembly.

13. The system of claim 12, wherein the suction assembly comprises a first pump-like unit connected to an outlet of the measurement unit.

14. The system of claim 13, wherein the suction assembly comprises a second pump-like unit interconnected between the region of interest and an inlet of the measurement unit.

15. The system of claim 14, wherein the first and second pump-like units are operable synchrony to provide a desired flow of the sample medium through the measurement unit.

16. The system of claim 9, wherein the feeding unit comprises a sample preparation unit connectable to the sensor unit.

17. The system of claim 16, wherein the sample preparation unit is configured as a separator for separating and filtering out a purified air medium and collecting particles from the sample medium and flowing the collected particles to the measurement unit.

18. The system of claim 9, wherein the feeding unit comprises a sample preparation unit connectable to the measurement unit.

19. The system of claim 16, wherein the sample preparation unit comprises a pre-concentrate for collecting the sample medium, and a heating unit for heating the sample medium.

20. The system of claim 9, configured for identifying one or more substances in a liquid medium.

21. The system of claim 20, wherein the sensor unit comprises two measurement units configured such that the first measurement unit is located outside the liquid medium during the system operation and is capable of identifying one or more foreign substances in a vapor coming from said liquid medium, and the second measurement unit is driven for movement into and out of the liquid medium and is capable of identifying one or more foreign substances in the liquid medium.

22. The system of claim 1, wherein the compartments are arranged in a one-dimensional array.

23. The system of claim 1, wherein the sensor unit is a two-unit assembly configured to enable operation of one sensor unit during regeneration of the other.

24. The system of claim 1, configured for identifying one or more substances in a liquid medium.

25. The system of claim 24, comprising a lift-like assembly associated with the measurement unit for moving the measurement unit into and out of the liquid medium.

26. The system of claim 1, wherein the sensor element is a piezoelectric crystal resonator characterized by a certain resonance frequency value and carrying reactive molecules of a kind capable of interacting with said at least one foreign material to yield a reaction product that effects a change in the resonance frequency of said crystal resonator from said certain resonance frequency value, said change being indicative of the identity of said at least one foreign material.

27. The system of claim 26, wherein said piezoelectric crystal resonator is configured as an inverted mesa structure having a membrane-like region.

28. The system of claim 26, wherein said crystal resonator is a quartz crystal.

29. The system of claim 27, wherein the membrane-like region is coated with metal electrodes on opposite sides thereof.

30. The system of claim 26, wherein the crystal resonators of different sensor elements are modified with different reactive molecules, thereby enabling detection of various foreign materials.

31. The system of claim 26, comprising a control system connectable to the sensor unit and configured and operable for actuating the crystal resonators, measuring the change in the resonance frequency of the crystal resonators, and generating measured data indicative of the identity of said at least one foreign material.

32. The system of claim 1, configured for identifying one or more foreign materials carried by a person, the system comprising a gate having side and top walls defining the region of interest inside the gate, said gate carrying on its side and top walls a plurality of the sensor units such that the sensor units are exposed to air medium of the region of interest.

33. The system of claim 32, wherein the gate is formed with air outlets formed in the side and top walls thereof, the sensor unit being mounted in the vicinity of the respective air outlets to be thereby exposed to air medium of the region of interest.

34. A sensor unit comprising at least one measurement unit and at least one heating unit, each measurement unit comprising a plurality of sensor elements each configured and operable to be responsive to at least one foreign substance in the vicinity thereof and to generate a response signal indicative thereof, wherein: each of the sensor elements is mounted in its own compartment having an inlet and an outlet thus defining an environmental region in the vicinity of said sensor element separated from the surroundings of the compartment and from other compartments in said measurement unit, thereby increasing concentration of a sample medium drawn through the at least one heating unit for inspection by each of the sensor elements, and wherein the plurality of compartments are arranged in a spaced-apart relationship along a predetermined path, and wherein said at least one heating unit is configured and located for heating the sample medium while flowing towards the measurement unit.

35. A sensor unit according to claim 34 as one of said certain number of the sensing units, the sensor unit further comprising:
an additional measurement unit configured and operable to be responsive to at least one foreign material in its surroundings and generating a response signal indicative thereof,
a drive assembly associated with one of the measurement units for movement moving it into and out of a liquid medium,
a sample feeding unit configured and operable for providing a flow of vapor from said liquid medium towards and through the other measurement unit.

36. A sensing system for use in identifying at least one foreign substance in a region of interest, the sensing system comprising a certain number of sensor units, each sensor unit comprising at least one measurement unit and at least one heating unit, each measurement unit comprising an array of sensor elements each configured and operable to be responsive to at least one foreign substance in the vicinity thereof and to generate a response signal indicative thereof, wherein each of the sensor elements is mounted in its own compartment having an inlet and an outlet thus defining an environmental region in the vicinity of the sensor element separated from the surroundings of the compartment and from the other compartments containing the other sensor elements in said measurement unit, thereby increasing concentration of a sample medium to be inspected when supplied to each of the sensor elements, and wherein the plurality of compartments are arranged within the measurement unit in a spaced-apart relationship along a circular path with respect to an inlet of the measurement unit to provide substantially concurrent supply of the sample medium to all the sensor elements and provide uniform distribution of the sample medium between all the compartments for inspection by the sensor elements accommodated in said compartments; and said at least one heating unit being configured for carrying out at least one of the following: heating the sample medium while flowing towards the measurement unit, and heating inner surfaces of the sensor unit to prevent adsorption of the sample medium thereon.

37. A sensing system for use in identifying at least one foreign substance in a region of interest, the sensing system comprising:

a certain number of sensor units, each sensor unit comprising at least one measurement unit and at least one heating unit, each measurement unit comprising: a plurality of sensor elements each configured and operable to be responsive to at least one foreign substance in the vicinity thereof and to generate a response signal indicative thereof, wherein each of the sensor elements is mounted in its own compartment having an inlet and an outlet thus defining an environmental region in the vicinity of the sensor element separated from the surroundings of the compartment, the compartments being arranged within the measurement unit in a spaced-apart relationship along a circular path with respect to an inlet of the measurement unit to provide uniform distribution of the a sample medium drawn through the at least one heating unit into the inlet of the measurement unit and concurrently supplied to all the compartments for inspection by the sensor elements accommodated in the compartments; said at least one heating unit being configured for carrying out at least one of the following: heating the sample medium while flowing towards the measurement unit, and heating inner surfaces of the sensor unit to prevent adsorption of the sample medium thereon; and a feeding unit configured and operable for providing an input flow of a sample medium from the region of interest towards and through the heating and measurement unit.

38. A sensing system for use in identifying at least one foreign substance in a region of interest, the sensing system comprising a certain number of sensor units, each sensor unit comprising at least one measurement unit and at least one heating unit, each measurement unit comprising: a plurality of sensor elements each configured and operable to be responsive to at least one foreign substance in the vicinity thereof and to generate a response signal indicative thereof, wherein each of the sensor elements is mounted in its own compartment having an inlet and an outlet thus defining an environmental region in the vicinity of the sensor element separated from the surroundings of the compartment, thereby increasing concentration of a sample medium in the vicinity of the sensor element inside the compartment, and wherein the compartments are arranged in a linear array; said at least one heating unit being configured and located for heating the sample medium while flowing towards the measurement unit.

39. A sensing system for use in identifying at least one foreign substance in a region of interest, the sensing system comprising:

a certain number of sensor units, each sensor unit comprising at least one measurement unit and at least one heating unit, each measurement unit comprising a plurality of sensor elements each configured and operable to be responsive to at least one foreign substance in the vicinity thereof and to generate a response signal indicative thereof, wherein each of the sensor elements is mounted in its own compartment having an inlet and an outlet thus defining an environmental region in the vicinity of said sensor element separated from the surroundings of the compartment and from the other compartments, wherein the compartments are arranged in a spaced-apart relationship in a linear array, a sample medium being sequentially supplied to all the compartments; said at least one heating unit being configured and located for heating the sample medium while flowing towards the measurement unit;

and a feeding unit configured and operable for providing an input flow of the sample medium from the region of interest towards and through the heating and measurement units.

40. A sensing system for use in identifying at least one foreign substance in a region of interest, the sensing system comprising:

a certain number of sensor units, each sensor unit comprising at least one measurement unit, each measurement unit comprising: a plurality of sensor elements each configured and operable to be responsive to at least one foreign substance in the vicinity thereof and to generate a response signal indicative thereof, wherein each of the sensor elements is mounted in its own compartment having an inlet and an outlet thus defining an environmental region in the vicinity of the sensor element separated from the surroundings of the compartment and from the other compartments, thereby increasing concentration of a sample medium to be inspected in the compartment; said at least one heating unit being configured and located for heating the sample medium while flowing towards the measurement unit; and a feeding unit configured and operable for providing an input flow of a sample medium from the region of interest towards and through the measurement unit, the feeding unit comprising a sample preparation unit connectable to the sensor unit, the sample preparation unit comprising a pre-concentrate for collecting the sample medium.

* * * * *